(12) United States Patent
Tooley (10) Patent No.: US 8,021,612 B2
(45) Date of Patent: Sep. 20, 2011

(54) SYSTEM AND METHODS FOR ASSISTING BUSINESSES IN COMPLIANCE WITH GAS EMISSIONS REQUIREMENTS

(76) Inventor: Jamie Tooley, Yucaipa, CA (US)

( * ) Notice: Subject to any disclaimer, the term of this patent is extended or adjusted under 35 U.S.C. 154(b) by 823 days.

(21) Appl. No.: 11/566,653

(22) Filed: Dec. 4, 2006

(65) Prior Publication Data

US 2007/0224085 A1 Sep. 27, 2007

Related U.S. Application Data

(60) Provisional application No. 60/786,442, filed on Mar. 27, 2006.

(51) Int. Cl.
*G01N 15/06* (2006.01)
*G01N 33/00* (2006.01)
*G01N 33/48* (2006.01)
*G01N 21/00* (2006.01)
*G01N 31/00* (2006.01)
*B01D 50/00* (2006.01)
*B01D 53/34* (2006.01)
*F01N 3/00* (2006.01)
*F23J 11/00* (2006.01)
*G05B 21/00* (2006.01)

(52) U.S. Cl. ......... 422/68.1; 422/67; 422/168; 700/266; 700/273

(58) Field of Classification Search .................... 422/67, 422/68.1, 168
See application file for complete search history.

(56) References Cited

U.S. PATENT DOCUMENTS

| 6,169,962 B1 | 1/2001 | Brookshire et al. |
| 2002/0150516 A1 * | 10/2002 | Pahlman et al. ............... 422/171 |

FOREIGN PATENT DOCUMENTS

WO     WO 03/103864 A1     12/2003

OTHER PUBLICATIONS

Phone interview itinerary for Apr. 27, 2011.*
Search Report for Application No. GB 0701914.4, filed Jan. 31, 2007.

* cited by examiner

*Primary Examiner* — Sam P Siefke
*Assistant Examiner* — Bryan T Kilpatrick
(74) *Attorney, Agent, or Firm* — Knobbe Martens Olson & Bear LLP (57) ABSTRACT

A system and method for calculating a value indicative of the amount of an undesirable constituent of a volatile gas stream that is removed from the atmosphere. Data received at a higher sampling rate is subjected to a plurality of validation processes and data that is determined to be faulty is then quarantined. Quarantined data can be replaced, however, an audit trail is generated to indicate what data has been replaced and the underlying rationale for the replacement data.

15 Claims, 6 Drawing Sheets

SYSTEM AND METHODS FOR ASSISTING BUSINESSES IN COMPLIANCE WITH GAS EMISSIONS REQUIREMENTS

RELATED APPLICATION

This application claims the benefit of U.S. Provisional Patent Application No. 60/786,442, filed Mar. 27, 2006, which is hereby incorporated by reference in its entirety herein.

BACKGROUND OF THE INVENTION

1. Field of the Invention

The present invention relates to systems for automatically capturing data relating to the removal of undesired constituents from volatile gases and, in particular, concerns a system which automatically collects data relating to the removal of carbon from volatile gases, such as greenhouse gases, validates the data and then determines the quantity of gas destroyed and the resultant amount of gaseous carbon reduced.

2. Description of the Related Art

In this era of global warming, the reduction of greenhouse gases and, in particular, the reduction of carbon containing gas in the environment is highly desirable. To this end, many countries of the world have entered into the Kyoto Protocol which requires countries to reduce the amount of greenhouse gas emissions and, in particular, reduce the amount of gases that contain carbon. This will require that certain industries and facilities that produce carbon containing gases take steps to reduce the amount of carbon containing gas emissions that they are releasing into the atmosphere. In addition to the Kyoto Protocol, various national governments have also implemented or are contemplating implementing procedures whereby various industries are provided with incentives to reduce the greenhouse emissions and the emissions of carbon containing gases.

Under the Kyoto Protocol, it is contemplated that industries will be given credits for the quantifiable amount of carbon that they have removed from the atmosphere. It is believed that these carbon credits will ultimately be traded between industries and will assume monetary value. Similarly, the United States contemplates providing tax credits to industry for the amount of carbon containing gases that have been reduced or otherwise removed from the atmosphere. These regimes have made it desirable to be able to accurately determine the amount of carbon gases that have been removed from the atmosphere.

However, in some implementations, it is often very difficult to determine the amount of carbon that have been removed from the atmosphere. One particular example of such a difficult implementation involves landfills. Landfills typically include a considerable amount of organic material that is decomposing underground. Volatile carbon containing gases, such as methane, are often produced as a result of this decomposition process. If allowed simply to vent into the atmosphere, the amount of carbon contained in these gases can be substantial.

As a consequence, it is desirable to prevent as much of the carbon containing gases, such as methane, from landfills from venting into the atmosphere. Typically, landfills will have a plurality of wellheads that are positioned so as to capture the gases and the well heads are often linked together such that the gases are provided to one or more destruction devices. The destruction devices can, in the simplest implementation, be a furnace or flare that is lit which results in the volatile carbon containing gases burning thereby transforming a fraction of the gaseous carbon component into solid carbon which thereby removes it from the atmosphere.

As the decomposition process within a landfill is variable, it is often difficult to determine with a high level of certainty for any particular time interval the amount of volatile carbon gases that have been reduced. The constituent components of the volatile carbon gases will vary based upon the materials that are decomposing and the volume of the volatile carbon containing gases will also vary based upon a wide variety of factors. As a consequence, it is necessary to monitor the gas flow and constituent components of the gas flow as well as the performance of the device used to reduce the volatile carbon gases on a fairly frequent basis to make an assessment of the amount of carbon that has been removed from the atmosphere.

Consequently, the monitoring system for such variable carbon gas producing facilities, such as landfills, is necessarily complex and involves many highly sophisticated and sensitive sensors. As a result of the complexity of the sensing system, it is not uncommon that various components will render faulty readings from time to time. Given the variability of the amount of gases being produced and also being reduced, faulty components for a particular period of time can result in a substantial loss of data and an inability to determine the actual amount of carbon that had been removed out of the atmosphere during certain time periods.

Generally, when data necessary for the calculation of the amount of carbon that has been removed from the atmosphere is missing, approximations of the data are often manually made by individuals. However, this manual approximation is often done on an ad hoc basis which reduces the confidence in the accuracy of the reported amount of carbon that has been reduced out of the atmosphere. In systems where compensation is going to be provided for this data, this loss of accuracy and confidence in the data can have a significant effect on the willingness of people to give monetary amounts for credits given for claimed carbon reduction.

Specifically, without some type of a verifiable system that is able to determine or approximate the faulty data, the willingness of government agencies to provide tax credits for carbon removed or reduced is going to be lessened. Moreover, if credits are going to be exchanged on an open market, the underlying basis and method of determining the credits has to be sufficiently accurate and transparent so as to justify a level of confidence on the part of the participants in the market.

Based upon the foregoing, there is a need for a system that will monitor the amount of carbon reduced out of greenhouse gases in systems that are subject to high variability in the amount of gas flow and the gas component, such as in landfill-type systems. To this end, there is a need for a system which is able to correct for missing or faulty data in a manner that is transparent and allows for subsequent review to thereby increase the confidence that auditors and other interested parties will have in the resulting figures relating to the amount of carbon that has been reduced or removed from the atmosphere.

SUMMARY OF THE INVENTION

The aforementioned needs are satisfied, in one aspect, by a system for monitoring a highly-variable carbon gas source. In one particular implementation, the system includes a first monitoring system which measures the characteristics of the carbon gas and the characteristics of the reduction device reducing the volatile gas into a less volatile form on a frequent basis. The system further includes memory devices that captures historical records of the gas characteristics and reduction characteristics. The system further compares data as it is received to the historical data in order to determine whether the received data may be erroneous. When the system determines that the received data may be erroneous, the data is then quarantined and an individual then has the opportunity to determine whether to replace the quarantined data with replacement data. The system is advantageously configured such that when such replacement occurs, the rationale for such replacement is recorded such that upon subsequent audit or review of the data, the rationale for the replaced data can be reviewed and audited.

In one particular implementation, the data is subjected to a plurality of different verification steps. In one particular implementation, the plurality includes verifying that the data falls within preset minimum and maximums and that further the plurality includes determining whether the data falls within a threshold deviation from an average value of previously obtained data. In yet another implementation, the system further includes monitoring on a less frequent basis gas flows and constituent components of the gas at locations other than the destruction device and then calculating a correlated value that correlates to the value that is received on the more frequent basis. In this particular implementation, the verification can include comparing the more continuously received data to the calculated correlated data from the distributed gas flow and determining whether the more continuously captured data is within a preset amount of the correlated, calculated data.

From the foregoing it will be appreciated that the system and method disclosed herein provide for a more verifiable calculation and also a calculation whereby faulty data can be replaced but the replaced data is more easily subject to review and auditing. As such, the data can be used for calculations of the amount of the undesirable gas component that has been removed from the atmosphere with greater confidence to thereby allow for more confidence in basing financial transactions on the data. These and other objects and advantages of the present invention will become more apparent from the following description taken in conjunction with the accompanying drawings.

DETAILED DESCRIPTION OF THE PREFERRED EMBODIMENT

Figure 1:
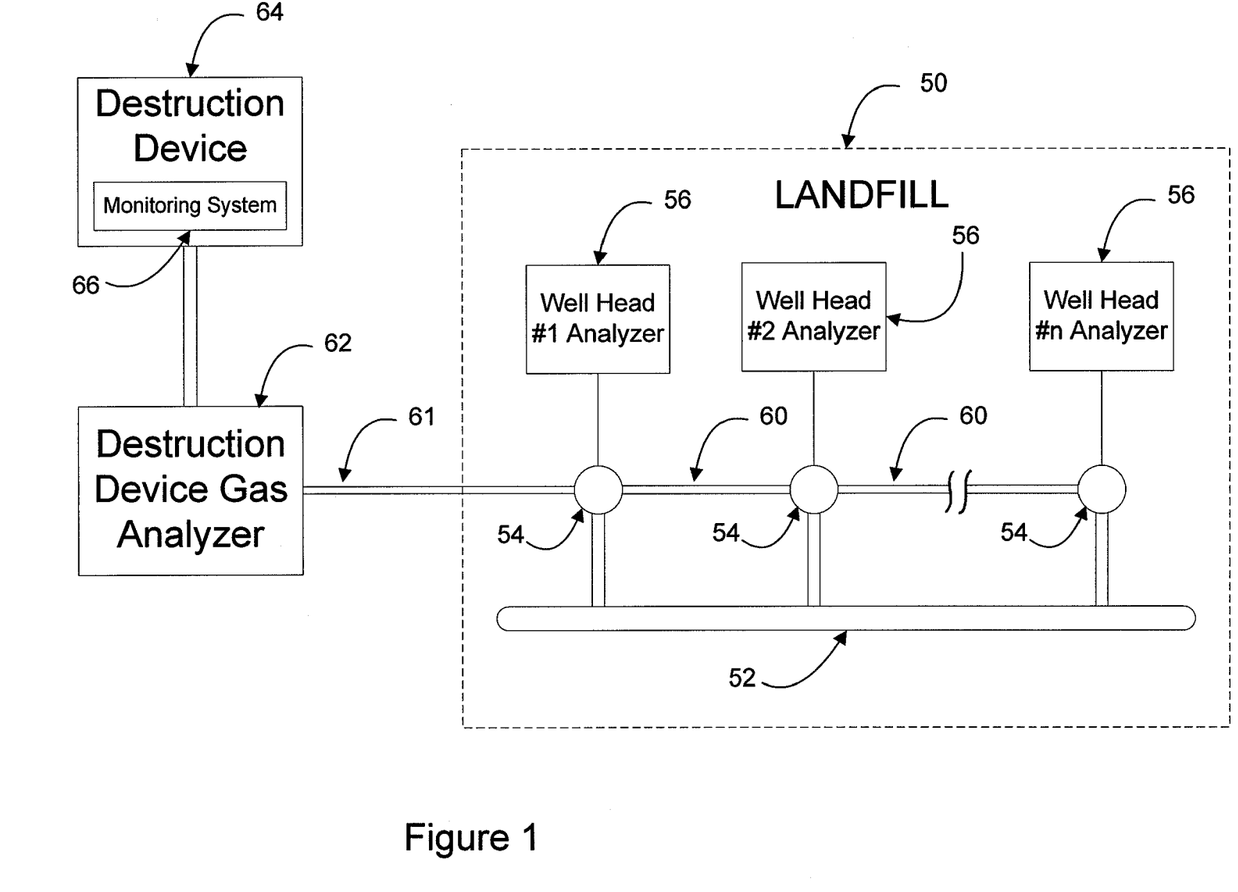
FIG. 1 is a schematic illustration of a system for capturing data off of a variable volatile gas source such as a landfill.

Reference will now be made to the drawings wherein like numerals refer to like parts throughout. Referring initially to FIG. 1, a system for capturing and reducing undesirable components of volatile gases off of a variable volatile gas source is illustrated. In this particular implementation, the variable volatile gas source is a landfill which has a distributed quantity of decomposing organic material 52 that is buried underneath the ground. The exact composition of the decomposing material 52 varies widely as does the rate of decomposition as well as the constituent components of the decomposition. Volatile gases, such as methane, are produced as a result of the decomposing material 52 and the land fill 50 is thus equipped with a plurality of well heads 54 that are used to capture the volatile gases from the decomposing material 52. The amount, number and size of well heads will, of course, vary greatly depending upon the actual implementation. In this particular embodiment, a plurality of well head analyzers 56 are also installed on at least some of the well heads and the well head analyzers 56 measure such things the flow rate and the constituent components of the volatile gases read at a particular well head. In one particular implementation, the well head analyzers record an aggregate amount of gas that has flowed over a preselected period, e.g., over a day, multiple days or a week, as well as the gas pressure and gas composition also detected during the same time period. One exemplary well head analyzer 56 that can be used is an Accu-flo well head analyzer, GEM-type analyzer, manufactured by LANDTEC of Colton, Calif. As is also indicated in FIG. 1, the well heads 54 are linked together via gas transportation systems 60 such that the volatile gases containing the undesirable constituents can be aggregated together and provided to a destruction device 64. The destruction device is a device that is adapted to remove the undesirable constituents out of the gas flow. The destruction device 64 can comprise such things such as scrubbers, filters, furnaces and flares. In one particular common implementation, the destruction device 64 comprises a flame burner or flare to which the volatile gas is provided such that the volatile gas can then be burned which results in at least a portion of volatile carbon gas being transformed into solid carbon and thereby removed from the atmosphere.

In order to determine the quantity of undesirable constituents, e.g., carbon components in the volatile gas stream that is removed, the aggregate volatile gas is fed into a destruction device gas analyzer 62 which monitors characteristics of the volatile gas flow including such things as the volume, rate and pressure of gas flow, as well as other characteristics, such as the temperature of the gas flow and the constituent components or the composition of the gas flow including, for example, the amount of volatile carbon containing gases. A typical destruction device gas analyzer 62 that can be used in this particular implementation includes an FAU-type gas analyzer, available from LANDTEC of Colton, Calif.

As will be discussed in greater detail below, the destruction device gas analyzer 62 preferably samples the gas flow at a relatively high frequency, e.g., once every two minutes, and generates a signal indicative of the volatile gas flow at this relatively high sampling rate. As will be discussed in greater detail below, this data can then be used to determine the amount of undesirable constituents in the volatile gas flow that has been reduced as a result of the operation of the destruction device.

As is also indicated in FIG. 1, the destruction device further includes a monitoring system 66 that monitors the characteristics of the destruction device such that the characteristics of the destruction device can be used to calculate the amount of the undesirable constituents that have been reduced out of the gas flow. In one particular implementation, the destruction device 64 comprises a flare and the monitoring system comprises a plurality of sensors that measures such things such as the heat energy produced when the volatile gas is burned as well as the constituents components of the gas flow residing following the burning of the volatile gas being supplied from the volatile gas source 50. In one particular implementation, the monitoring system 66 includes an FSU-type monitoring system, available from LANDTEC of Colton, Calif.

Hence, the system disclosed in FIG. 1 comprises a system which accumulates a volatile gas flow that has some undesirable constituents, such as carbon and then provides this to a destruction device which is designed to remove at least a portion of the undesirable characteristics and the system further includes a plurality of different sets of sensors that measure data indicative of the characteristics of the gas flow at different locations and possibly different sampling rates. It will be appreciated that the exact configuration of the system for accumulating, assessing, and reducing volatile gas flows with undesirable constituents can, of course, vary greatly depending upon the implementation without departing from the spirit of the present teachings.

Figure 2:
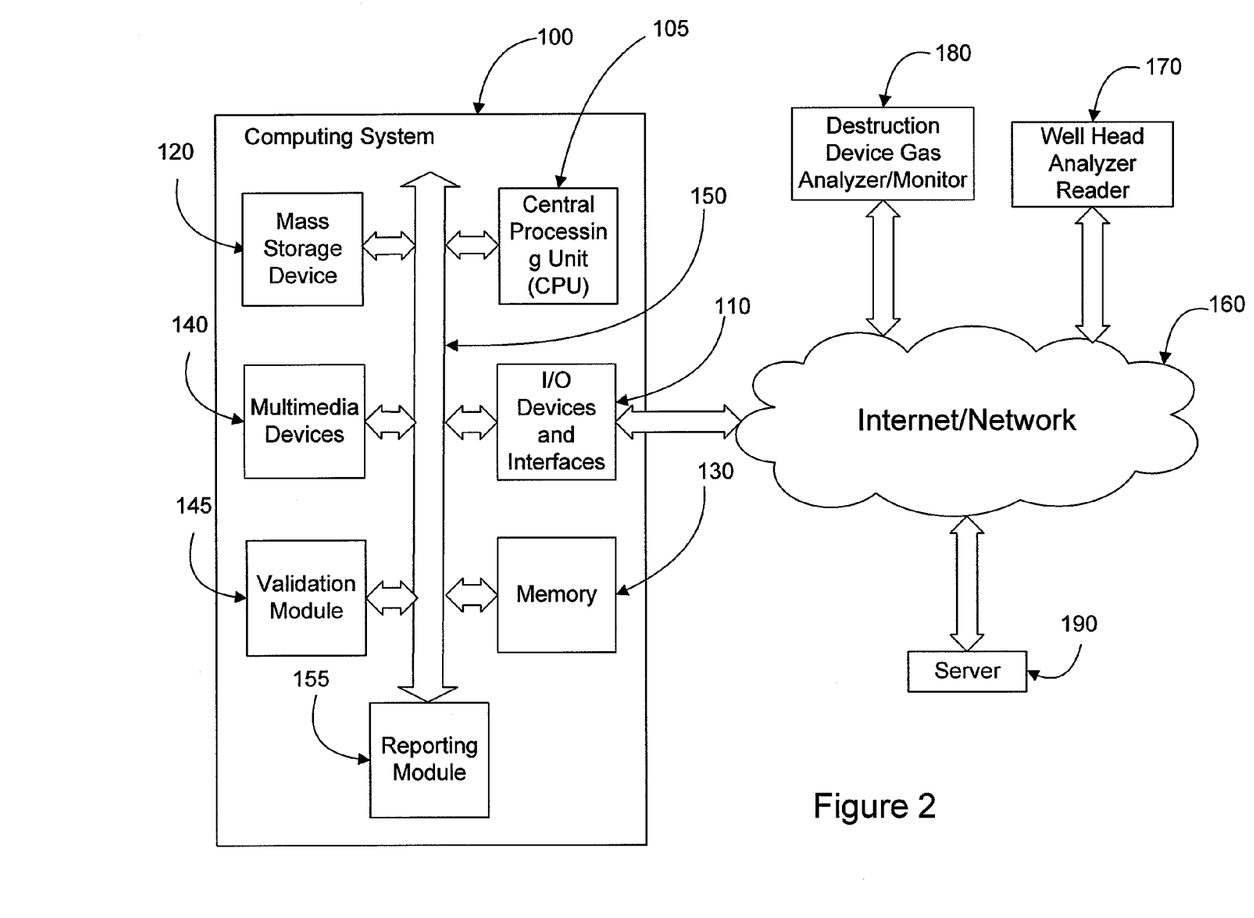
FIG. 2 is a schematic illustration of a system for calculating and verifying the amount of undesirable constituents in the gas that has been removed by the system of FIG. 1.

FIG. 2 is an exemplary block diagram illustrating the system by which a calculated quantity of undesirable constituents in the volatile gas flow is determined. This particular system comprises a computer-based system 100 and can include, for example, a personal computer that is IBM, Macintosh, or LINUX/UNIX compatible. In one embodiment, the exemplary computing system 100 includes a central processing unit 105 that may include a conventional microprocessor. The computing system 100 further includes a memory 130 such as a Random Access Memory (RAM) for temporary storage of information, a Read Only Memory (ROM) for permanent storage of information, a mass storage device 120 such as a hard drive, diskette or optical media storage device.

The mass storage device 120 includes such data as previously captured data that is stored in a well known manner. The previously captured data can then be used to validate newly received by though comparison of historical averages, most recent averages and the like.

Typically, the modules of the computing system 100 are connected to the computer using a standard based bus system. In different embodiments, the standard based bus system can include peripheral component interconnect (PCI), micro channel, SCSI, Industrial Standard Architecture (ISA), and Extended ISA (EISA) architectures, for example. The computing system 100 is generally controlled and coordinated by operating system software such as Windows 95, 98, NT, 2000, XP, LINUX, SUN OS, Solaris, or other compatible operating systems. In Macintosh systems the operating system may be any available operating system such as MAC OSX. In other embodiments, the computing system 100 may be controlled by a proprietary operating system. Conventional operating systems control and schedule computer processes for execution, perform memory management, provide file systems, networking and IO services, and provide a user interface, such as a Graphical User Interface (GUI) among other things.

The exemplary computing system 100 includes one or more commonly available Input/Output (I/O) devices and interfaces 110, such as a keyboard, mouse, touchpad and printer. In one embodiment, the I/O device and interfaces include one or more display devices, such as a monitor, that allows the visual presentation of data to a user. More particularly, a display device provides for the presentations of GUI's, application software data, and multimedia presentations, for example. The computing system 100 may also include one or more multimedia devices 140, such as speakers, video cards, graphic accelerators and microphones, for example.

In the embodiment of FIG. 2, the I/O devices and interfaces 110 provide a communications interface to various external devices. In the embodiment of FIG. 2, the computing system 100 is coupled to a network 160 such as a LAN, WAN, or the Internet, for example via a wired, wireless or combination of wired and wireless communications links 115. The network communicates with various computing devices and/or other electronic devices via wired and wireless communications links. In the exemplary embodiment of FIG. 1, the computing device 100 communicates with the destruction device gas analyzer 62 and the monitoring system 66 for the destruction device via the network. Similarly, readers that read the well head analyzer 56 can also provide the data to the computing system 100 via the network. The system further includes a server 190 that is attached to the computing system 100 also via the network.

Hence, the computing system 100 is capable of receiving data indicative of the volatile gas flow from not only the destruction device gas analyzer 62 and the associated destruction device monitoring system 66, but can also receive data taken from each of the well head analyzers 56 using a well head data analyzer monitor 170 such as a GEM-type monitor available from LANDTEC. While this data is indicated in FIG. 2 as being provided via the Internet or network, it will also be appreciated that this data can be provided to the computing system 100 in a variety of different formats including such things as by manual input of the data at an I/O device, physical transportation of a reader from the well head analyzers to the computing systems, paging and text messaging without departing from the spirit of the present teachings.

As is also indicated in FIG. 2, the computing system 100 is logically organized to include a validation module 145 that receives the data from the destruction device gas analyzer 62, associated destruction device monitor 66, as well as the data from the well head analyzer reader 170 and then performs various validation processes on the received data in order to validate that the data being received by the computing system 100 is a valid representation of the actual physical conditions occurring at the destruction device 64. Moreover, the computing system 100 is also logically organized to include a reporting module 155 that provides reports indicative of the performance of the destruction device 64 and the gas flow which can then be used to determine the quantity of undesirable constituents, such as carbon-based constituents, that have been removed from the volatile gas flow as a result of the operation of the destruction device 64. The manner in which the validation module 145 and the reporting module 155 operate will be described in greater detail below in conjunction with the description associated with the flow charts of FIGS. 3-6. detail below in conjunction with the description associated with the flow charts of FIGS. 3-6.

Figure 3:
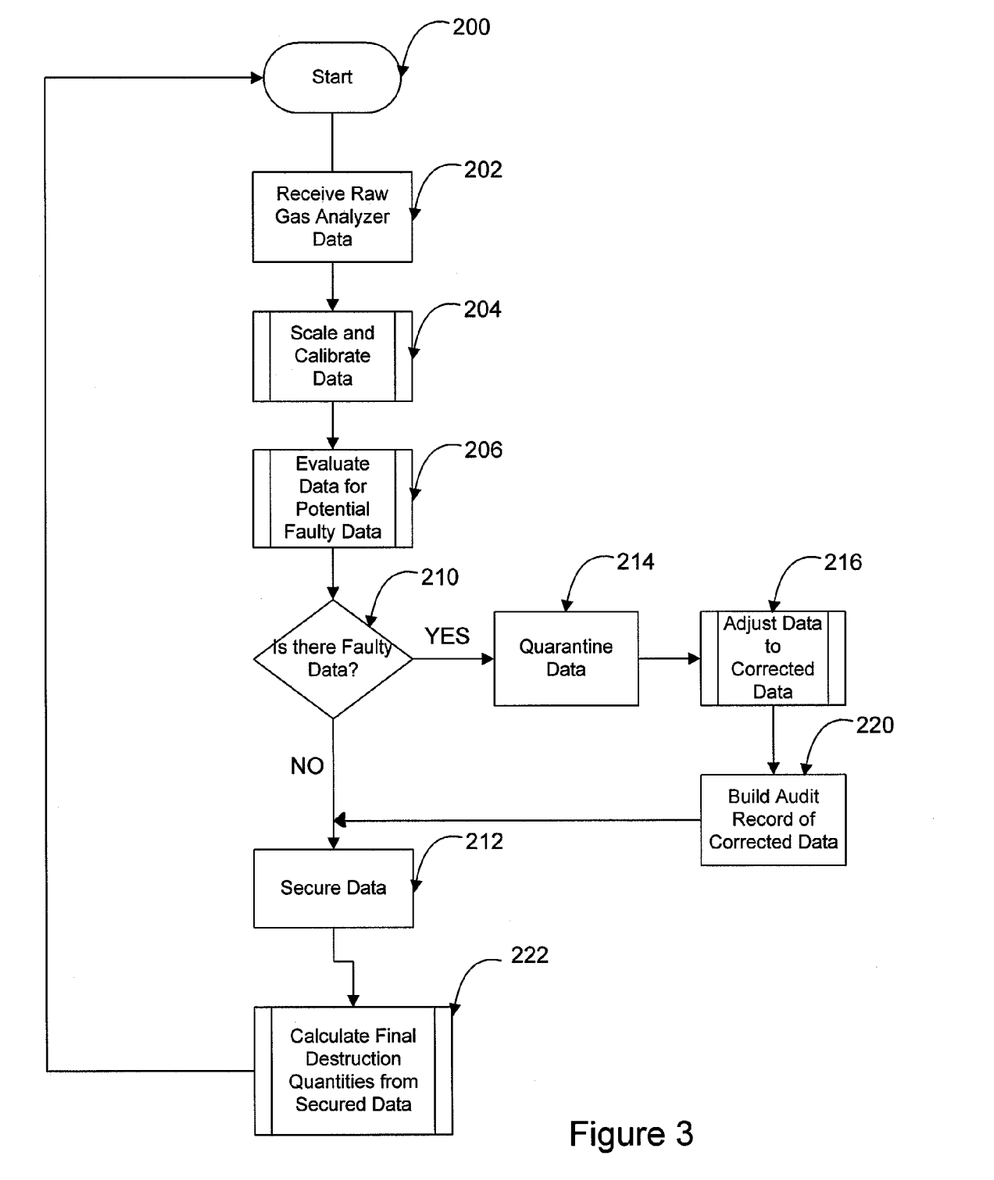
FIG. 3 is an exemplary flow chart illustrating a process flow by which the amount of undesirable constituents in the gas flow that have been reduced out of the atmosphere is determined, verified, and used to calculate a quantified value corresponding thereto.
Figure 4:
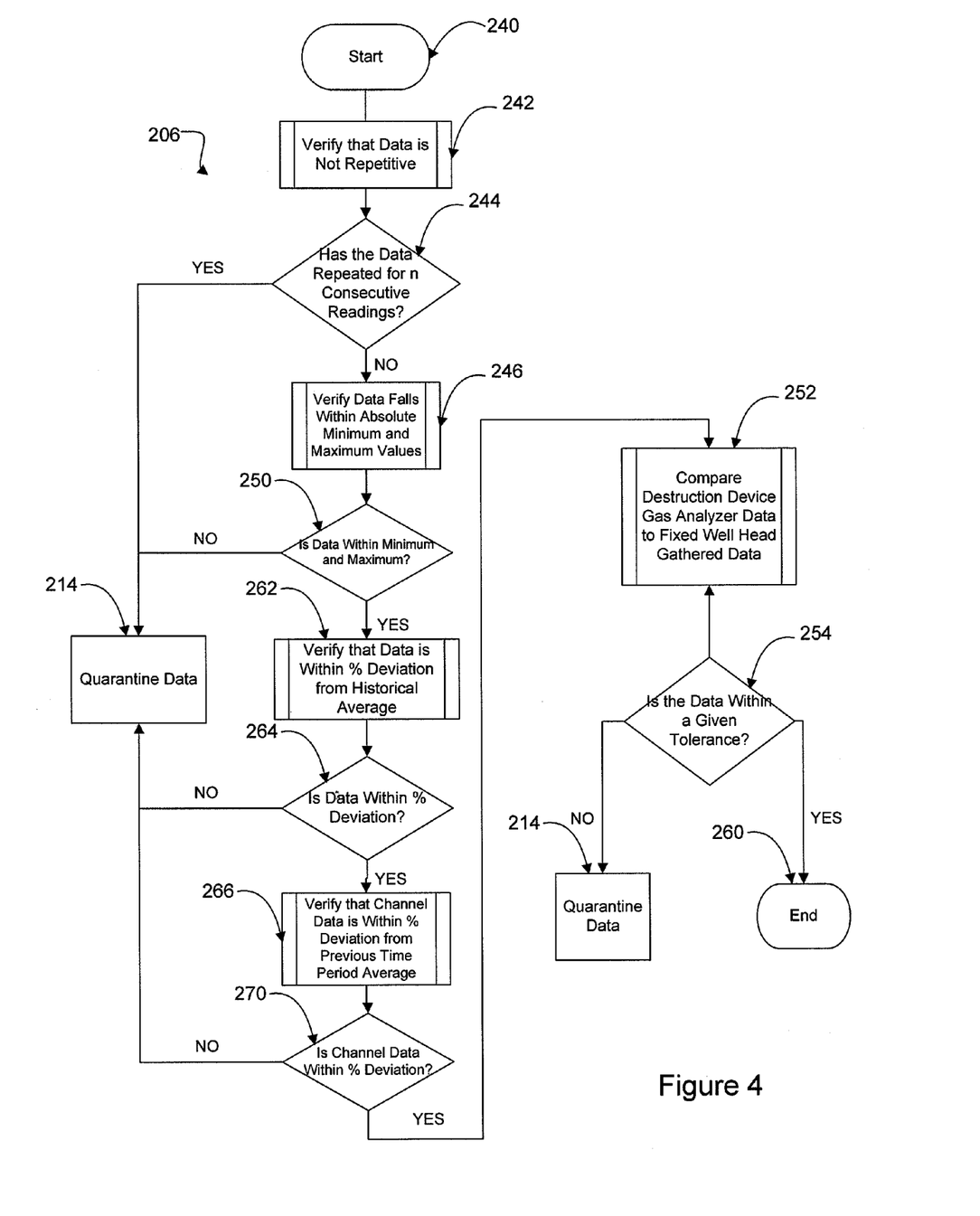
FIG. 4 is an exemplary flow chart illustrating the manner in which the data received from the volatile gas source is verified.
Figure 5:
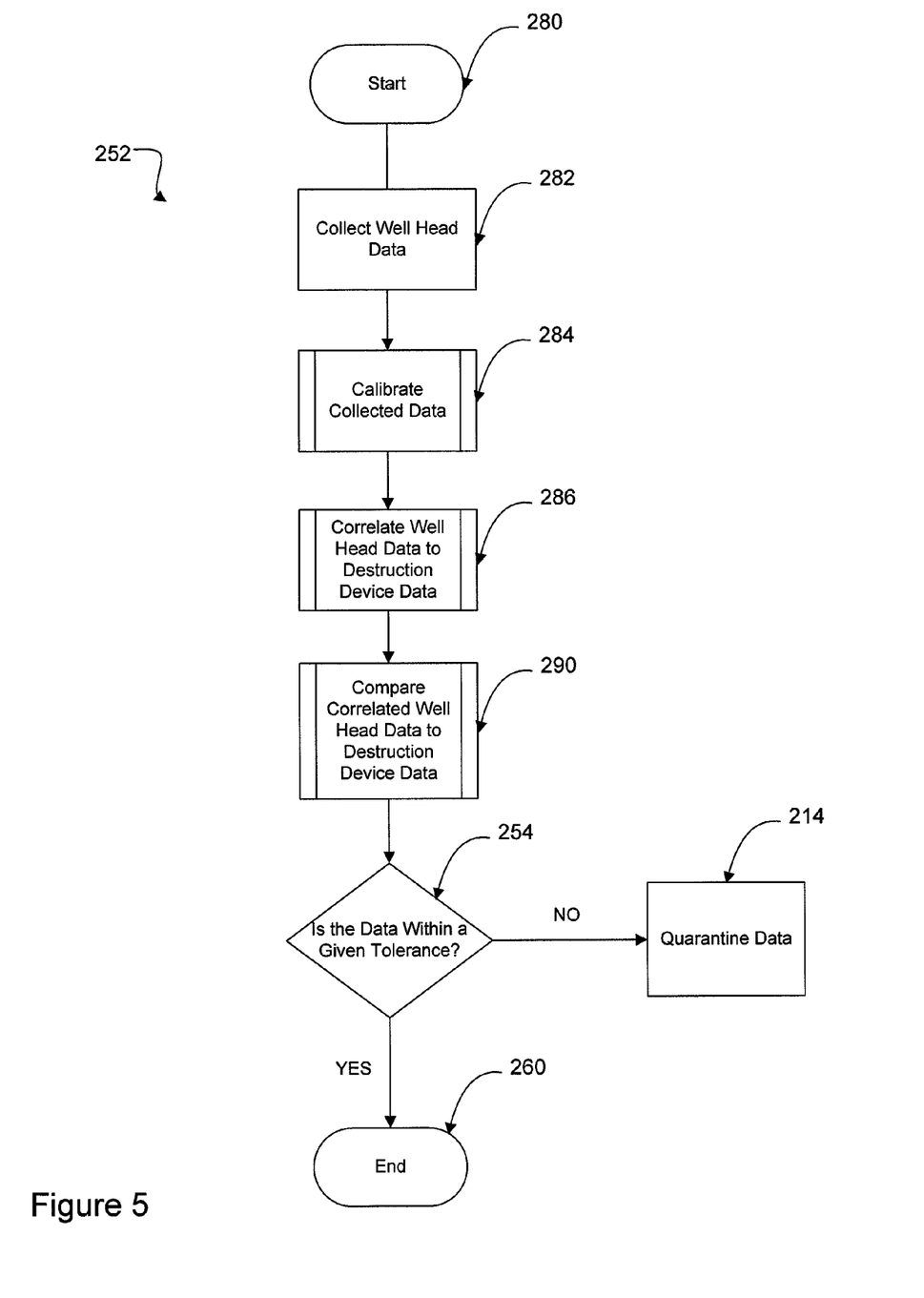
FIG. 5 is an exemplary flow chart illustrating one possible verification process whereby centrally collected data is compared to correlated, distributed collected data in the volatile gas source.
Figure 6:
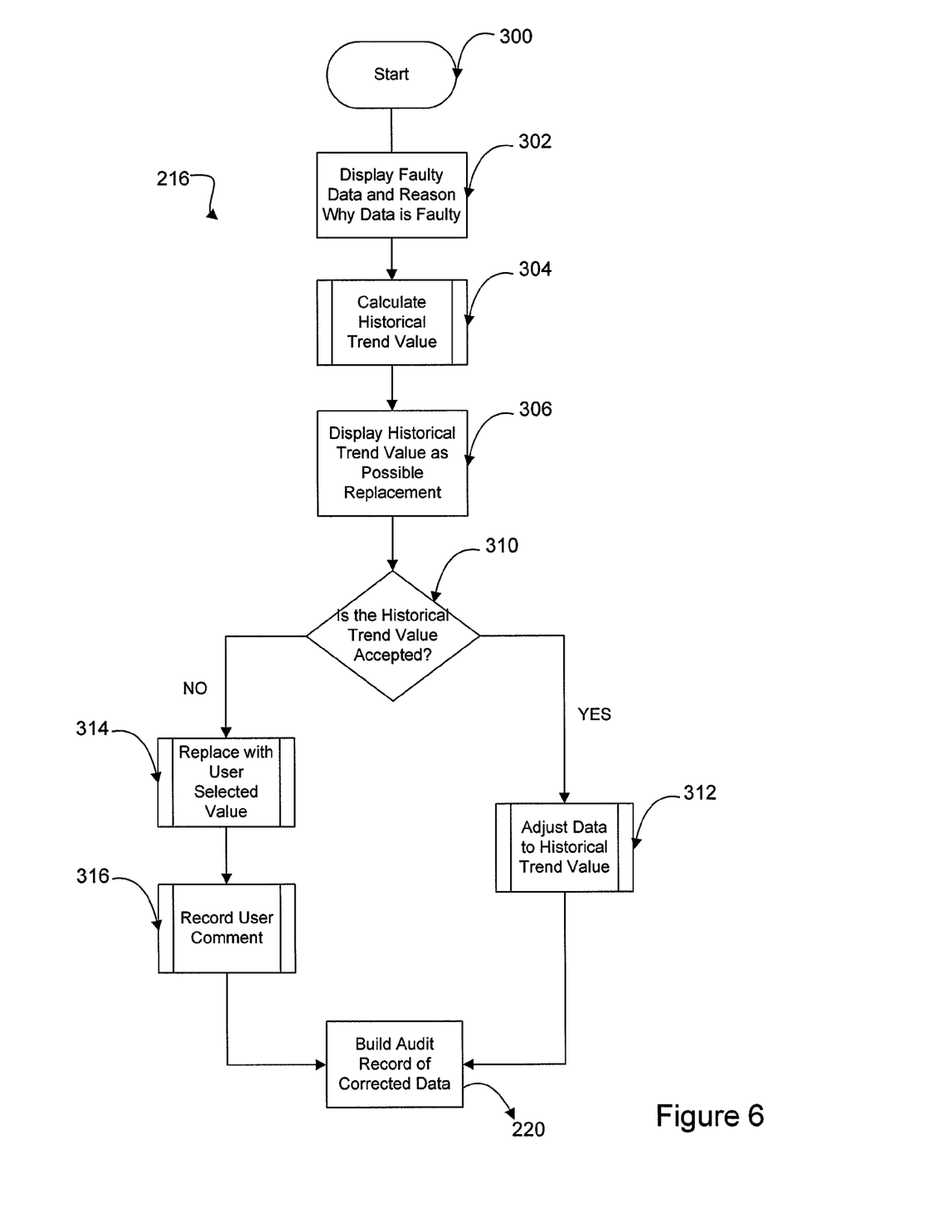
FIG. 6 is an exemplary flow chart illustrating the manner in which faulty data is replaced with predictive data and the process whereby such changes are recorded for subsequent review and auditing purposes.

FIG. 3 is a flow chart that illustrates the operation of the computer system 100 as it verifies the data that is received from the destruction device gas analyzer 62 and the monitoring system 66 of the destruction device. It will be appreciated that the flow chart of FIG. 3 along with the flow charts of FIGS. 4-6 are illustrative of the functional operation of the computer system 100, however, the sequence of steps and the implementation of the steps themselves can, of course, vary depending upon the particular implementation without departing from the spirit of the present invention and that the flow charts are thus simply exemplary and not limiting to the teachings contained herein. Referring to FIG. 3, the computer system 100, from a start state 200, receives the raw gas analyzer data in state 202. In general, the raw gas analyzer data is provided either through hardware connections, a network connection or wireless connection from the gas analyzer 62 and destruction device monitoring system 66 in any of a number of well-known formats. Preferably, this data is received on a near continuous basis during operation of the destruction device 64 at a relatively high sampling rate such that a near continuous record of the gas that is being produced by the landfill and the resultant destruction is substantially continuously monitored. In one particular implementation, the gas analyzer 62 and the monitoring device 66 provide data indicative of the amount, pressure and rate of gas flow, the constituent components of the gas flow, heat and burn characteristics of the gas in the destruction device 64 and residual gases following the burning of the volatile gas. In one implementation, this information is sampled every two minutes. It will, however, be appreciated that faster or slower sampling rates may be implemented depending upon the degree of variability of the volatile gas being produced by the source of the desired level of precision of the resulting measurements.

Once the raw data has been received, the raw data is then scaled and calibrated in State 204. As will be appreciated from the following discussion, the raw data is going to be converted into quantities that can be used for comparative analysis. As such, scale factors provided by the manufacturer of the gas analyzer 62 and monitoring system 66 will have to be employed to scale the data. Further offset compensation values will generally be applied to the raw data in order to end up with a data set that is comparable to previously or subsequently obtained data. The scaling and compensation of the raw data will generally be accomplished using any of a number of well-known scaling and compensating techniques.

Once the data has been scaled and calibrated, the scaled and calibrated data is then evaluated, in state 206, for potential faulty data. As will be described in greater detail below, a plurality of different validations processes are performed on the calibrated data in order to determine whether the data that is being received is faulty. Faulty data can stem from a variety of different circumstances, including faulty or clogged sensors, changed environmental conditions, communications failures and the like. Hence, recognizing data that is falling outside of historical norms, expected thresholds or doesn't coincide with other corresponding data, is suggestive of faulty data which can result in erroneous calculations for the amount of carbon that has been removed from the atmosphere. The various processes by which the faulty data will be determined in state 206 will be described in greater detail below in conjunction with the flow chart of FIG. 4.

If the system determines, in decision state 210, that there is suspected faulty data, the faulty data is preferably quarantined, in state, 214, by the computer system 100 to thereby allow a human operator to review the potentially faulty data to determine whether it is in fact faulty data and also to take steps to replace the faulty data with replacement data that is likely to more accurately represent the actual conditions in the gas analyzer 62 and monitoring system 66.

Hence, a human operator will periodically, e.g., hourly, daily, etc., review the quarantined data and make a determination as to whether the quarantined data is faulty and, if it is faulty, will then replace the faulty data with corrected data in state 216. The corrected data can either be data that is empirically determined, e.g., the average of historical data for similar type conditions, or can be data that is calculated based upon other parameters received by the computer system 100, such as the data received from the well head analyzers 56.

Further, the corrected data may also comprise data that is selected by the human operator based upon the human operator's experience. The manner in which the corrected data will be determined to replace the faulty data will be described in greater detail below in conjunction with the flow charts of FIGS. 5 and 6.

Advantageously, each time that the quarantined data is deemed to be faulty and it is replaced, the computer system 100 builds an audit record in state 220. Preferably, the audit record includes what the original data was, as well as the replaced corrected data and a comment provided by the human operator that is preferably indicative of why the data was deemed to be faulty and also the rationale as to why particular values for corrected data was selected. In this way, a verifiable record can be kept of the corrected data and underlying rationales which allows for subsequent audits and further allows the auditors to determine whether the rationale for selecting a particular corrected value for the data was reasonable. Presumably, an auditor could identify the selected data, disagree with the rationale for selecting a particular corrected data, substitute new corrected data and then recalculate the ultimate final values. Hence, building the record of the data that has been deemed to be faulty and also a record of what the faulty data has been replaced by and the underlying rationale allows for greater transparency and instills greater confidence in the final calculated values.

The non-faulty data and the corrected data are preferably stored in state 212 in the mass storage device 120 (FIG. 2). In this way, a complete record of the data can be preserved. Following the storing of the data in state 212, the system 100 then calculates, in state 222, the final destruction quantities from the secured data. The calculation of the final destruction quantities can be done according to a wide variety of algorithms, but preferably follow a standard set of algorithms that is generally accepted by others in the industry to provide the best indication as to the amount of undesirable constituents in the volatile gas flow that has been removed. The calculation determining the amount of carbon that has been removed from the gas flow out of the landfill can follow any of a know set of formulas. The final destruction quantities that are calculated are generally calculated on a periodic basis, e.g., daily, weekly, and the like.

FIG. 4 is an exemplary flow chart that illustrates the verification process that is performed on the calibrated data in function 206. It will be appreciated from the following description that a wide variety of different verification steps can be performed and that the data verification steps that are performed in this particular implementation are simply exemplary of the various types of verification steps that can be implemented.

From a start state 240, the system 100 initially determines whether the data is repetitive. Data on any of the channels that have substantially the same value for a large number of samplings is indicative of perhaps a faulty sensor that is no longer able to track the variations in the particular measurement. As a consequence, the system 100 keeps a counter of consecutive identical readings on any particular channel. If the system 100 determines, in decision state 244, that the data has repeated for a selected number of consecutive readings, the data is then quarantined in state 214 to be processed in the manner described above. If the data has not repeated for a preselected number of consecutive readings, the system 100 then verifies, in state 246, whether the data falls within preselected absolute minimum and maximum values for the particular data. In general, for a particular parameter, such as gas flow, there is predetermined minimum and maximum value that can be expected out of the gas source based upon empirical historical observations of the gas source. Hence, the system 100 in state 246 compares each of the incoming data values to a minimum and maximum for that particular value. If the system 100 determines in decision state 250 that the data is not within the preselected minimum and maximum values, then the data is quarantined in state 214 and is evaluated by the human operator in the manner described above.

If the data is within the minimum and maximum values, the computer system 100 then verifies, in state 262, whether the data is within a preset percentage deviation from the historical average for that particular parameter. The percentage deviation will, of course, vary depending upon the particular parameter in question and also depending upon the particular landfill in question. Even for highly variable gas sources, substantial deviations from the historical average may provide an indication that the data is suspect thereby necessitating a further review of the data to determine whether it is faulty or not. If the system 100 determines, in decision state 264, that the data on a particular channel corresponding to a particular parameter deviates more than a preselected percentage amount, the data can then be quarantined in state 214 to be reviewed by a human operator in the manner described above.

Subsequently, the system 100 then verifies that the data is within a preselected average that has been recorded in a recent previous time period. For each time period, e.g., each week, an average for that particular week is preferably calculated by the system 100 and stored. Subsequently, during the next time period, the data during the next time period can be compared to the data during the previous time period to see if there is a substantial deviation. It will be appreciated that in many systems, there will be deviations over the course of the year based upon environmental factors and the like. By comparing the currently received data to what has been received in the previous time period, substantial deviation can be indicative of faulty data. Hence, if the system 100 determines in decision state 270 that the current values being received from the gas analyzer and monitoring system substantially deviate from the averages that have been received during a selected preceding time period, then the data is quarantined in state 214 for further review by the human operator in the manner described above.

If the data is within an acceptable deviation of the previous averages, the system 100 then proceeds to compare the destruction device gas analyzer data to corresponding values determined from the well head analyzer 56 in function 252. More specifically as will be described in greater detail below in reference to FIG. 5, the well head data analyzers 56 provide summary data corresponding to the total gas flow, the total value of constituent components and the like over a substantially longer time period, e.g., one day, one week, etc. This particular information can then be used to calculate generally expected averages that correspond to the sampling rate at which the system 100 is receiving the data from the destruction device gas analyzer 62 and the monitoring system 66.

If the system 100 determines that there is a substantial deviation between the more frequently sampled data from the destruction device gas analyzer 62 and the values calculated from the well head analyzer data, then the data will be quarantined in state 214 for further review by the human operator in the manner described above. If the currently sampled data is within a tolerance value of the expected value determined from the well head analyzers, the system 100 proceeds to an end state 260 and proceeds with the flow described above in connection with FIG. 3.

Referring now to FIG. 5, the process by which the computer system 100 compares the destruction device gas analyzer data to well head gathered data (state 252—FIG. 4) is illustrated in greater detail. As discussed above, the gas analyzer 62 is receiving the aggregate gas flow off of all of the well heads 54. On each well head 52 there is a well head analyzer 56 that is also measuring gas flow and, in some implementations, constituent components of the gas flow. In general, the well head analyzers 56 in this particular implementation are obtaining aggregate records of the amount of gas flow and the amount of constituent components in the gas flow over a preset period of time. As this data is being captured independent of the data that is being captured on a more frequent basis in the destruction device gas analyzer 62, this data provides a basis for checking the validity of the data captured by the destruction device gas analyzer 62.

Referring specifically to FIG. 5, from a start state 280, the well head data 282 has to be periodically collected. In one particular implementation, an individual goes out to each well head analyzer 56 and obtains a reading of the collected data with the well head analyzer reader 170 (FIG. 2) which is then provided to the computer system 100 in any of a variety of means including wireless transmission, wire transmission or direct transfer of data via data storage media such as disks and the like.

Once the well head data is collected, the data has to be calibrated in state 284 in a manner that is known in the art. Once the data has been calibrated, the data must be correlated to the destruction device data in state 286. In this particular implementation, the well head analyzer data is being sampled at a substantially slower rate than the destruction device gas analyzer data which makes comparisons between the two difficult. Hence, the well head analyzer data must thus be correlated such that values correspond to the values that would be expected to be seen by the destruction device gas analyzer 62 which is sampling the data at a much higher sampling rate. In one implementation, the aggregate data is processed into an average value for the corresponding sampling rate of this destruction device gas analyzer data. Once this correlation is done, a comparison between the correlated well head data and the destruction device data can be made in state 290 and the computer system 200 can then determine, in decision state 254, whether the data was in a given tolerance in the manner described above in connection with FIG. 4. Hence, the more real time collected data from the destruction device gas analyzer 62 can be independently verified against aggregate data that is being collected the well head analyzers 56 which comprise an independent data capture system.

Thus, the system 100 employs a plurality of different data validation techniques in order to ensure that the data that is being sampled by the destruction device gas analyzer 62 and destruction device monitoring system 66 is valid data that can then be used for the calculation of the amount of carbon that is destroyed. Such multiple levels of validation provide destruction quantity numbers that are more reliable, as discussed above. Moreover, if any one of the plurality of data validation techniques determines that particular data is faulty, the data can then be quarantined and replaced in the manner described above in connection with FIG. 3. More specifically, FIG. 6 illustrates one exemplary process 216 whereby the faulty data can be replaced by more reliable inferred data.

Specifically referring to FIG. 6, from a start state 300, the computer system initially displays the faulty data on a graphical user interface for the human operator to review. Preferably, an indication as to why the data is faulty, e.g., which validation test the data failed, is also displayed to the human operator.

The computer system 100 also calculates a historical trend value in state 304 that corresponds to the quarantined data that is being displayed to the human operator in state 306. The historical trend value can be any of a number of different types of values including historical averages, averages that are weighted based on environmental conditions or most recent trend-type averages. Once the historical trend value has been calculated, it is displayed to the human operator in state 306 as a possible replacement.

The computer system 100 then determines in decision state 310 whether the historical trend value has been accepted and, if it has been accepted, and if it has been accepted it adjusts the quarantined data to the historical trend value in state 312 and increments the audit record in state 220 in the manner described above. If the human operator does not accept the historical trend value, the system then proceeds to state 314 wherein the faulty data can be replaced with user selected values, however, the user selected values are not recorded in the audit record until a user comment is recorded is state 316. Thus a verifiable record can be developed by the reporting module 155 which can be subsequently accessed for auditing and subsequent verification purposes.

Hence, the foregoing system describes a system whereby more accurate data can be captured and faulty data can be replaced with reasonable inferred data such that more reliable end calculations can be performed. This allows for more accurate calculations of such things as total carbon destroyed or total carbon removed from the atmosphere by a landfill destruction device.

Although the above disclosed embodiments of the present invention have shown, described and pointed out the fundamental novel features of the invention as applied to the above-disclosed embodiments, it should be understood that various omissions, substitutions and changes in the form of the detail of the devices, systems and/or methods illustrated may be made by those skilled in the art without departing from the scope of the present teachings. Consequently, the scope of the invention should not be limited to the foregoing description but should be defined by the appended claims.

What is claimed is:

1. A system for monitoring and recording removal by a removal device of undesired constituents of a gas produced by a variable gas source, the system comprising:
    at least one gas sensor that senses characteristics of the gas and provides gas signals indicative of the characteristics of the gas before removal of undesired constituents from the gas;
    at least one removal device sensor that senses characteristics of the removal device as the removal device removes undesired constituents of the gas and provides removal signals indicative of operation of the removal device;
    a computing system comprising a computer readable medium storing software code for execution by the computing system in order to perform operations comprising accessing the gas signals and the removal signals;
    using the gas signals and the removal signals to develop a first record that corresponds to a quantity of undesired constituents removed from the gas;
    verifying data developed from the gas and removal signals;
    in response to determining that the data is faulty, permitting replacement of the faulty data with replacement data; and
    in response to receiving replacement data, developing a second record indicative of the replacement data as well as a rationale for selection of the replacement data.

2. The system of claim 1, wherein the gas sensor comprises a gas analyzer that is adapted to sense characteristics of a volatile carbon containing gas and wherein the computing system develops the first record which is indicative of an amount of carbon that has been removed from the atmosphere by a destruction device after processing the volatile carbon containing gas.

3. The system of claim 2, wherein the characteristics of the volatile carbon containing gas include characteristics indicative of a flow rate of the gas and composition of the gas.

4. The system of claim 2, wherein the gas sensor provides signals indicative of the gas at a high frequency sampling rate.

5. The system of claim 4, wherein the high frequency sampling rate comprises a sampling rate of once every approximately 2 minutes.

6. The system of claim 1, wherein the removal device sensor senses heat energy of the removal device and residual constituent components of the gas remaining after the gas has been introduced to the removal device.

7. The system of claim 1, wherein the computing system performs a plurality of validity checks on the gas signals and the removal signals to determine whether the signals being received are indicative of valid data.

8. The system of claim 7, wherein the plurality of validity checks include comparing the data developed from the gas and removal signals to pre-selected minimum and maximum values for particular data.

9. The system of claim 7, wherein the plurality of validity checks include comparing the data developed from the gas and removal signals to corresponding average values calculated from previously received corresponding data.

10. The system of claim 9, wherein the average is a historical average over the operation of the recording system.

11. The system of claim 9, wherein the average is determined from a previously occurring recent period of time.

12. The system of claim 4, further comprising a plurality of sensors that sense flow of gas at a plurality of distributed locations at a second sampling rate that is less than the high frequency sampling rate, and wherein the plurality of validity checks include developing data from the plurality of sensors that correlates to the data developed from the gas signal and comparing the data to determine if the data corresponds.

13. The system of claim 1, wherein the computing system verifies the data by performing at least one validity check and if the at least one validity check indicates that the data is potentially faulty, the data is then quarantined for review by a human operator who can then replace the faulty data.

14. The system of claim 13, wherein the computing system calculates potential replacement data for the quarantined data based upon previously received data.

15. A non-transitory computer-readable storage medium having code stored thereon that, in response to execution by a computing device, cause the computing device to perform operations comprising:
    receiving gas signals indicative of the characteristics of the gas before removal of undesired constituents from the gas;
    receiving removal signals indicative of operation of a removal device;
    accessing the gas signals and the removal signals;
    using the gas signals and the removal signals to develop a first record that corresponds to a quantity of undesired constituents removed from the gas;
    verifying data developed from the gas and removal signals;
    in response to determining that the data is faulty, permitting replacement of the faulty data with replacement data; and
    in response to receiving replacement data, developing a second record indicative of the replacement data as well as a rationale for selection of the replacement data.

* * * * *